United States Patent [19]

Taraschi et al.

[11] Patent Number: 5,631,278
[45] Date of Patent: *May 20, 1997

[54] METHODS OF KILLING PROTOZOAL PARASITES

[75] Inventors: Theodore F. Taraschi, Tabernacle, N.J.; Bruno Pouvelle, Charbonnieres, France

[73] Assignee: Thomas Jefferson University, Philadelphia, Pa.

[*] Notice: The term of this patent shall not extend beyond the expiration date of Pat. No. 5,356,927.

[21] Appl. No.: 448,422

[22] PCT Filed: Dec. 2, 1993

[86] PCT No.: PCT/US93/11668

§ 371 Date: Aug. 31, 1995

§ 102(e) Date: Aug. 31, 1995

[87] PCT Pub. No.: WO94/12172

PCT Pub. Date: Jun. 9, 1994

Related U.S. Application Data

[63] Continuation-in-part of Ser. No. 9,131, Jan. 26, 1993, abandoned, which is a continuation-in-part of Ser. No. 984,915, Dec. 2, 1992, Pat. No. 5,356,927.

[51] Int. Cl.$^6$ .................................................. A61K 31/335
[52] U.S. Cl. ................................................................ 514/449
[58] Field of Search ................................................ 514/449

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,356,927 | 10/1994 | Taraschi et al. | 514/449 |

OTHER PUBLICATIONS

Baum, S. et al., "Taxol, a Microtubule Stabilizing Agent, Blocks the Replication of *Trypanosoma cruzi*", PNAS USA 1981, 78(7), 4571–4575.

Denis, J.-N. et al., "Direct, Highly Efficient Synthesis from (S)–(+)–Phenylglycine of the Taxol and Taxotere Side Chains", *J. Org. Chem.* 1991, 56, 6939–6942.

Dieckmann–Schuppert, A. et al., "Mode of Action of Tubulozoles Against *Plasmodium falciparum* In Vitro", *Antimicrobial Agents adn Chemotherapy* 1990, 34(8), 1529–1534.

Fuerst, R., Chapter 41 in "Frobisher and Fuerst's Microbiology in Health and Disease", Chap. 41, W. B. Saunders Company, 1983, USA, pp. 600–605.

Kaminsky, R. et al., "Feeder Layer–free In Vitro Assay for Screening Antitrypanosomal Compounds Against *Trypanosoma brucei* brucei and *T. b. evansi*", *Chemical Abstracts* 1989, 111, Abstract, No. 53655j.

Kumar, N. et al., "*Plasmodium gallinaceum*: Critical Role for Microtubules in the Transformation of Zygotes into Ookinetes", *Exp. Parasitol.* 59(2), 239–247 in Embase Abstract No. 85110113 1985.

Singleton, P. et al., "Dictionary of Microbiology and Molecular Biology", (2nd Ed.) John Wiley & Sons, New York, 1987, pp. 239, 468, 494, 688, 790 and 898.

*Primary Examiner*—Raymond Henley, III
*Attorney, Agent, or Firm*—Woodcock Washburn Kurtz Mackiewicz & Norris

[57] ABSTRACT

Methods of inhibiting the proliferation of protozoal parasites employing taxol or taxol analogs are provided by the present invention. Such methods may be useful for treating such infections in mammals such as humans.

6 Claims, 8 Drawing Sheets

METHODS OF KILLING PROTOZOAL PARASITES

CROSS REFERENCE TO RELATED APPLICATIONS

This application is a U.S. national phase entry of PCT Application No. PCT/US93/11668, filed Dec. 2, 1993, which is a continuation-in-part of U.S. Ser. No. 08/009,131, filed Jan. 26, 1993, now abandoned, which is a continuation-in-part of U.S. Ser. No. 07/984,915, filed Dec. 2, 1992, which issued on Oct. 18, 1994 as U.S. Pat. 5,356,927.

BACKGROUND OF THE INVENTION

Protozoans infect and kill millions of people annually. However, in most cases, efficacious chemotherapeutic agents and vaccines are unavailable to treat these diseases.

Human malaria, caused by a protozoan sporozoa, is an acute and chronic protozoal disease caused by four species of plasmodia, namely *Plasmodium falciparum*, *P. vivax*, *P. ovale* and *P. malariae*. *P. falciparum* is the most virulent of these and the only one that kills acutely. The plasmodial parasites are transmitted by female mosquitoes of several species of the genus Anopheles. The World Health Organization recognizes malaria as the world's major primary health problem, causing more morbidity and mortality than any other disease. An estimated 300–500 million cases occur annually resulting in 3–5 million deaths, mostly among children. Malaria is a serious problem mainly in the tropical and subtropical world, especially Africa, South and Central America, India and Southeast Asia. Isolated cases of malaria have recently been reported in the southeastern and southwestern United States. The drug chloroquine is often used to treat malaria, however, the rapid spread of chloroquine-resistant *P. falciparum* and the lack of a malaria vaccine emphasizes the long-felt need to develop new strategies and agents for controlling this disease.

Babesiosis, an infection by protozoan sporozoa of the genus *Babesia*, is transmitted by hard-bodied ticks. The causative organisms, parasites resembling those of malaria, invade and destroy erythrocytes. *Babesia* infections in wild and domestic animals occur worldwide and are well known in veterinary medicine. Human infections are more rare and occur exclusively in Europe and North America. In many countries, Babesia is responsible for serious economic losses to the exclusively in Europe and North America. In many countries, *Babesia* is responsible for serious economic losses to the: livestock industry. No effective chemotherapeutic treatment or vaccine has been known for treatment of babesiosis.

Chagas disease (American trypanosomiasis) is a zoonotic infection caused by the protozoan *Trypanosoma cruzi*. It affects as many as 15 million people living in South and Central America. African Trypanosomiasis (Sleeping sickness) is a chronic infection with *Trypanosoma brucei gambiense* or an acute one with *T.B. rhodesiense*. These hemoflagellate protozoa are transmitted cyclically by several species of blood-sucking tsetse flies of the genus Glossind. There are no efficacious and safe drugs for treating the chronic forms of these infections.

Taxol is a diterpenoid isolated from the stem bark of the western yew, *Taxus brevifolia*. Taxol is a mitotic spindle poison that stabilizes microtubules and inhibits their depolymerization to free tubulin. Taxol has been demonstrated to possess antineoplastic activity and has been identified as an anti-cancer agent, particularly in the treatment of advanced ovarian cancer.

Over ten years ago, Baum et al. *Proceeding of the National Academy of Science, U.S.A.* 1981, 78, 4571–4575, found that taxol inhibited the flagellate protozoan *Trypanosoma cruzi*. Trypanosomes, being flagellated protozoans, belong to the protozoal Phylum mastigophora. Baum et al. found that the addition of taxol inhibited the replication of *T. cruzi* in a dose-dependent fashion. Baum et al. treated cultures containing trypanosomes with 1 µM to 10 µM of taxol. However, treatment of trypanosomiasis was never developed and there are presently no efficacious and safe drugs for treating these infections, particularly the chronic forms. Mastigophora, such as the *Trypanosoma* and *Leishmania* species, are flagellated protozoans that asexually reproduce by binary fission. This is quite different than the Protozoa Sporozoa, which includes the *Plasmodium*, *Toxoplasma*, *Isospora*, *Sarcocystis*, *Crytosporidium* and *Pneumocystis* species, which reproduce by asexual (schizogony) and sexual (sporogony) multiplication. Another important distinguishing feature of the Mastigophora from the Sporozoa is the unique microtubular cytoskeleton that lies just beneath the plasma membrane of the Mastigophora. Baum et al. suggested that it was the perturbation of this unique submembranous cytoskeletal network by taxol that prevented *Trypanosoma cruzi* daughter cells to separate during cytokinesis, thus blocking replication. The mode of action of taxol described by Baum et al. is not applicable to the Sporozoa for the reasons described above.

Treatments for malaria and babesiosis have been similarly disappointing. Methods which are known for the treatment of malaria and babesiosis have not been satisfactory due to expense, limited efficacy, drug resistance, and safety. Methods for the treatment of malaria and babesiosis infections are greatly needed. The present invention provides methods satisfying this long-felt need.

SUMMARY OF THE INVENTION

Treatment of protozoal diseases has been problematic due to the lack of effective agents which are at once inexpensive, efficacious, and safe. The currently available drugs used to treat malaria all act by similar mechanisms, i.e., acidification of the parasite's food vacuole or inhibition of parasite enzymes. Due to the chemical similarity of the agents (e.g., aminoquinolines or pyrimethamine), strains of *Plasmodium* have rapidly developed drug resistance and have created a need for new and novel methods of treating *Plasmodium* infections.

The present invention provides methods of inhibiting the proliferation of a *Plasmodium* parasite comprising contacting the *Plasmodium* parasite with an amount of taxol or taxol analog such as taxotere effective to inhibit the proliferation of said parasite.

The present invention provides methods of inhibiting the proliferation of a *Babesia* parasite comprising contacting the *Babesia* parasite with an amount of taxol or taxol analog such as taxotere effective to kill the parasite. The present invention also provides methods of treatment of other protozoal diseases such as *Leishmania*, Toxoplasmosis, Isosporosis, Sarcocystis, Pneumocystis and Cryptosporidiosis, by contacting the parasite with an amount of taxol or taxol derivative such as taxotere effective to kill the parasite.

The present invention further provides methods of inhibiting the proliferation of such protozoal parasites in a cell comprising contacting the cell with from about 0.1 µM to about 1 µM taxol or taxol analog such as taxotere.

The present invention also provides methods of treating protozoal infections in a mammal comprising administering to a mammal a therapeutically effective amount of taxol or taxol analog such as taxotere.

DETAILED DESCRIPTION OF THE INVENTION

The present invention provides methods of inhibiting the proliferation of protozoal parasites by contacting the parasite with an amount of taxol or taxol analog such as taxotere effective to inhibit the proliferation of the parasite. In other embodiments of the present invention the proliferation of such parasites in a cell may be inhibited by contacting the cell with from about 0.1 μM to about 1 μM taxol or taxol analog such as taxotere. In still other embodiments of the present invention, protozoal infections in a mammal can be treated by administering to a mammal suffering from such an infection a therapeutically effective amount of taxol or taxol analog such as taxotere.

The present invention provides methods of inhibiting the proliferation of protozoal parasites such as *Plasmodium*, *Babesia*, and *Trypanosoma*. Other protozoal diseases believed to be treatable with taxol and taxol analogs include Leishmania, Toxoplasmosis, Isosporosis, Sarcocystis, Pneumocystis carinii pneumonitis and Cryptosporidiosis.

Based upon ribosomal gene analysis, *Pneumocystis carinii* is now considered by some to be a fungus. However, it is considered by others to be somewhere between protozoa and fungi and is best considered as among the former. These diseases have been increasingly observed in AIDS patients and present new, problematic cases to clinicians. *Pneumocystis carinii* pneumonitis is the most common opportunistic infection in AIDS patients; it is the index diagnosis in 60% of AIDS patients in the United States and occurs at least once in an additional 20%. Cerebral toxoplasmosis occurs in about 1 in 6 or 7 American AIDS patients; it occurs more frequently in places with greater prevalence of positive serology to *Toxoplasma gondii*, e.g., France and most developing countries.

All of these protozoal parasites are known to possess cytoskeletal networks rich in tubulin. The mechanism by which taxol exerts it anti-malarial effects is unclear. In mammalian cells taxol functions as a mitotic spindle poison and is a potent inhibitor of cell replication in vitro. Sexual and asexual stages of *P. falciparum* contain microtubular structures which play a crucial role in nuclear division and parasite differentiation. However, it does not appear that taxol acts solely by preventing nuclear division or by directly killing parasites. A significant percentage of taxol treated IRBC were observed by electron microscopy to contain nucleated merozoites. In addition, taxol had little if any effect on DNA synthesis in mature parasites.

During the late stages of parasite intracellular development, individual uninucleate merozoites are formed in a synchronous manner by a budding process from a schizont. The merozoites develop with a rhoptry complex at the apical end by the progressive, outward evagination of the schizontal plasma membrane. The evaginated plasma membrane is associated with (and probably induced by) the development of an orderly array of tubules that originate from the apical end. Shaw and Tilney, *J. Cell Sci.*, 1992, 109, 109–123. These tubules progressively form a longitudinal basket enclosing first the rhoptry complex, and then the mitochondria, ribosomes and nucleus. Disruption of this process, as a result of taxol interfering with proper formation and functioning of the tubular network, could lead to the production of deformed, disorganized parasites that are unable to produce viable new infections. In accordance with this mode of action, taxol will have utility for treating other protozoan infections.

In addition, taxol appears to be more potent than classical antimalarials, since unlike chloroquine, it prevents the recrudescence of infection in vitro.

Taxol is commercially available or may be prepared such as by methods described by Holton, U.S. Pat. No. 4,876,399, issued Oct. 24, 1989; Colin et al., U.S. Pat. No. 4,814,470, issued Mar. 21, 1989; Colin et al., U.S. Pat. No. 4,857,653, issued Aug. 15, 1989; Holton, U.S. Pat. No. 5,015,744, issued May 14, 1991; and Denis et al., U.S. Pat. No. 4,924,011, issued May 8, 1990, the disclosures of which are incorporated by reference herein in their entirety. By the term taxol is also meant precursors, derivatives and analogs of taxol. All precursors, derivatives and analogs of taxol which are functionally interchangeable with taxol, yet structurally distinct are encompassed by the present invention. For example, water soluble derivatives of taxol are encompassed by the present invention. Some derivatives of taxol are described by Holton et al., U.S. Pat. No. 4,876,399 issued Oct.24, 1989; Haugwitz et al., U.S. Pat. No. 4,942,184 issued Jul. 17, 1990; Christen et al., U.S. Pat. No. 5,019,504, issued May 28, 1991; Kingston et al., U.S. Pat. No. 5,059,699, issued Oct. 22, 1991; and Stella et al., U.S. Pat. No. 4,960,790 issued Oct. 2, 1990, the disclosures of which are incorporated by reference herein in their entirety. Of course, any composition which binds to parasite microtubules thereby preventing proper spindle formation and nuclear division during schizogony could be effectively used in some methods of the present invention. The use of taxotere, a taxol analog is specifically contemplated by the invention.

In some embodiments of the present invention from about 0.1 µM to about 1 µM taxol or taxol analog such as taxotere effectively inhibits the proliferation of the parasites. Preferably 1 µM taxol or taxol derivative such as taxotere is contacted with the parasite. Cells infected with protozoal parasites may also be treated with from about 0.1 µM to about 1 µM taxol or taxol analog such as taxotere to eliminate or reduce the infection. In preferred embodiments of the present invention 10 to 100 times lower plasma concentrations of taxol will be therapeutically effective for the treatment of the disease than is necessary for antineoplastic treatment. Taxotere is 2–6 times more potent than taxol in inhibiting the replication of different cell lines in vitro. In preferred embodiments of the present invention, 20–600 times lower plasma concentrations of taxotere will be therapeutically effective. Therapeutically effective amounts are those amounts which reduce or eliminate an infection. Any reduction in the infection is therapeutic. Thus 10% of the parasites may be killed in accordance with some embodiments of the present invention. In preferred embodiments of the present invention a therapeutic or effective amount of taxol (or taxotere) effectively kills from about 50% to 100% of the parasites. In still more preferred embodiments at least 80% of the parasites are killed. In yet more preferred embodiments of the present invention at least 90% of the parasites are killed. In most preferred embodiments of the present invention 100% of the parasites are killed.

In some preferred embodiments of the present invention from about 0.01 µM to about 1.0 µM plasma concentration of taxol or taxol analog such as taxotere is envisioned for therapeutic treatment of such an infection in a mammal.

In more preferred embodiments of the present invention from about 0.05 µM plasma concentration of taxol or taxol analog such as taxotere to about 0.1 µM plasma concentration of taxol or taxol analog is envisioned for therapeutic treatment of the infection in a mammal.

One skilled in the art would also be familiar with methods of administration which may be effective for treatment of parasite infections in view of the present disclosure. For example, administration may be carried out intravascularly, intramuscularly, intraperitoneally, orally including via aerosol, rectally, etc., using a variety of dosage forms. In preferred embodiments of the present invention, taxol or taxol analog is administered by infusion. In some instances, it may be desirable to administer taxol or taxol analog in conjunction with other drugs or formulations. Thus, taxol or taxol analog may be administered bound to human serum albumin or encapsulated in liposomes in some embodiments of the present invention.

Treatment is performed until the desired therapeutic result, i.e., reduction or elimination of parasite infection, is achieved. Preferably, treatment is performed for from about 6 to about 48 hours. Treatment for the duration of from about 48 to about 144 hours may be effective in some embodiments of the present invention. In other embodiments of the present invention shorter durations may be useful, for instance, a single bolus may be sufficient in some cases to reduce or eliminate parasite infection.

One skilled in the art will recognize that the useful dosage, within the range identified, may be administered and the particular mode of administration, dosage, and duration will vary depending upon the age, weight and condition of the patient.

The following treatment regime is contemplated by the invention for the treatment of a variety of protozoal diseases. Taxol is supplied to the clinician as a concentrated sterile solution 6 mg/ml (7.02 mM) in a 5 ml ampule (30 mg/ampule), in polyoxyethylated castor oil (Cremophor EL), 50% and dehydrated alcohol USP, 50%. Prior to administration, the drug is further diluted in 1 liter of 5% dextrose in water, or 0.9% sodium chloride. In other formulations, taxol or taxotere are dissolved in ethanol, then polysorbate 80 is added and the final dilution of taxol or taxotere obtained with 5% glucose in water or 0.9% NaCl in water. On the basis of clinical observations, the National Cancer Institute recommends that patients be administered in a 24 hour infusions of taxol along with prophylactic antiallergic premedications (e.g., 20 mg dexamethasone orally 12 hours and 6 hours before taxol administration and 20 ml i.v. just before treatment; 50 mg diphenhydramine is given orally and i.v. per the same schedule as dexamethasone). Pharmacology studies have been preformed on patients with a variety of cancers who were infused continuously intravenously (i.v.) for 6 hours at a dose of 230 mg/m$^2$. Drug plasma concentrations increase throughout the 6 hour infusion and decline immediately after cessation of the infusion. Plasma disappearance curves are biphasic, with $\alpha$ and $\beta$ $t_{1/2}$ of 0.42 and 8.4 hours, respectively. Peak plasma concentrations ranged from 2–10 µM. Taxol binds extensively to plasma proteins (90–95%) and is systemically cleared by metabolism, biliary excretion and/or extensive tissue binding. The major side effects include neutropenia and hypersensitivity, which are manageable. These side effects can be controlled as dosage and duration of treatment are refined.

In preferred embodiments of the present invention, treatment of malarious patients is performed with from about a 6 to about a 24 hour i.v. infusion of taxol at from about 50 to about 250 mg/m$^2$ dose to alleviate the infection. In more preferred embodiments of the present invention a patient is administered from about 100 to about 200 mg/m$^2$ of taxol to alleviate the infection. In still more preferred embodiments of the present invention, a patient is administered about 150 mg/m$^2$ of taxol to alleviate the infection. Such treatment regime is advantageous. For example, In a 70 kg adult, a single treatment with taxol would require approximately 260 mg of drug. For comparison, to dosages of usual antimalarials, chloroquine is administered initially at 600 mg followed by 300 mg doses at 6, 24 and 48 hours. Quinine (700mg) is given i.v. every 8 hours or 700 mg orally t.i.d. Since a single treatment of taxol is likely to be efficacious even in drug-resistant strains, the side effects associated with long term administration in human cancer patients can be avoided.

The following examples are illustrative, but are not meant to be limiting of the present invention.

EXAMPLES

Example 1—Cultures

Different strains of cloned malaria parasites (FCR3-C5, ITG2-G1, Palo Alto, 3D7, HB3, 7G8, T9-94) were grown in tissue culture by the candle jar method at 5% hematocrit (FCR3-C5) or in Falcon tissue culture flasks gassed with 94% $N_2$, 5% $CO_2$, 1% $O_2$ at 3% hematocrit (ITG2-G1, Palo Alto, 3D7, HB3, 7G8, T9-94). The tissue culture medium consisted of RPMI 1640 supplemented with 24 mM $NaHCO_3$, 25 mMHepes, 21.1 mM dextrose, 2 mM glutathione, 0.44 mM hypoxanthine and 66 mg/l gentamycin and 10% heat-inactivated human serum. T9-94 is chloroquine resistant, 7G8 is chloroquine and pyrimethamine resistant and HB3 is pyrimethamine resistant. The drug resistant parasites were obtained from Dr. David Walliker at the University of Edinburgh, United Kingdom. Taxol, obtained from Molecular Probes, Inc., Eugene, Oreg. (Catalogue #T-3456) is dissolved in dimethyl sulfoxide (DMSO).

Example 2—Taxol treatment in vitro

Taxol, obtained from Molecular Probes, Inc., Eugene, Oreg. (Catalogue # T-3456) was dissolved in dimethyl sulfoxide (DMSO). Cultures of infected erythrocytes were either untreated, treated with DMSO only, or treated with taxol to a final concentration 0.01 µM, 0.05 µM, 0.1 µM, or 1.0 µM. All treated cultures contained the same final concentration of DMSO (0.17 %). Taxol was added to early ring stage IRBC (4–6 h post-invasion) infected with the P. falciparum clones FCR3-C5, T9-94, 7G8 or HB3, and maintained for 2 life-cycles. One cycle lasts 44–46 hours during which time intracellular parasites undergo asexual development and merozoites are released to produce new infections. The tissue culture medium was changed daily and a fresh aliquot of DMSO or taxol added as required. The initial parasitaemias of the cultures were 0.5–1.0%.

Example 3—Taxol

Taxol is supplied as a concentrated sterile solution 6 mg/ml (7.02 mM) in a 5 ml ampule (30 mg/ampule), in polyoxyethylated castor oil (Cremophor EL), 50% and dehydrated alcohol USP, 50%. Prior to administration, the drug is further diluted in 1 liter of 5% dextrose in water. On the basis of clinical observations, the National Cancer Institute recommends 24 hour infusions along with prophylactic antiallergic premedications (i.e., dexamethasone, diphenhydramine and cimetidine or ranitidine). Pharmacology studies have been performed on patients with a variety of cancers who were infused continuously intravenously (i.v.) for 6 hours at a dose of 230 mg/m². Drug plasma concentrations increase throughout the 6 hour infusion and decline immediately upon cessation of the infusion. Plasma disappearance curves are biphasic, with an $\alpha$ and $\beta t_{1/2}$ of 0.42 and 8.4 h, respectively. Peak plasma concentrations ranged from 2–10 µM. Taxol binds extensively to plasma proteins (90–95%) and is systemically cleared by metabolism, biliary excretion and/or extensive tissue binding. The major side effects at these dosages include neutropenia and hypersensitivity, which are manageable.

Example 4

Cultures of human erythrocytes infected with the FCR3-C5 (Gambian, chloroquine and pyrimethamine sensitive) clone of Plasmodium falciparum were grown in the absence and presence of taxol as described in Example 2. The infections were synchronized with sorbitol treatment to ±2 hours as described by Lambros and Vanderberg, J. Parasitol., 1979, 65, 418–420. Parasitemia was measured by examining Giemsa-stained blood smears using a light microscope. The efficacy of taxol, expressed as parasitemia is defined as the number of infected erythrocytes divided by the total number of erythrocytes X 100. The efficacy of taxol, expressed as parasitemia (% of control) was determined by counting the parasitemia in treated cultures 10 hours after invasion was completed in the control, untreated and DMSO-treated cultures and comparing it to the parasitemia of the untreated control cultures. A parasitemia of 0% indicate that taxol totally inhibits new infections; a parasitemia of 100% indicates that taxol has no effect. The parasitemia were calculated by pooling the results of two separate experiments, with 1000 cells counted at each taxol concentration. DMSO was determined to have no effect on parasite viability or invasion. Parasitemias were identical in untreated and DMSO treated cultures. Taxol reduced the parasitemia of the cultures in a dose dependent fashion. After one replication cycle, 0.5 µM and 1.0 µM taxol reduced the parasitemia by 95% and 100%, respectively. After two cycles, 0.5 µM totally eliminated parasitemia.

Example 5

Cultures of human erythrocytes infected with HB2. (Honduras, chloroquine sensitive, pyrimethamine resistant) clone of Plasmodium falciparum were grown in the absence and presence of taxol as described in Example 2. The infections were synchronized with sorbitol treatment to ±2 hours as described by Lambros and Vanderberg, J. Parasitol., 1979, 65, 418–420. The infections were synchronized with sorbitol treatment to ±2 hours as described by Lambros and Vanderberg, J. Parasitol., 1979, 65, 418–420. Taxol was added 4 hours post-invasion and maintained in cultures for three life cycles. Each life cycle is approximately 48 hours in duration. Parasitemia was measured by examining Giemsa-stained blood. smears using a light microscope. The efficacy of taxol, expressed as parasitemia is defined as the number of infected erythrocytes divided by the total number of erythrocytes X 100. The efficacy of taxol, expressed as Parasitemia (% of control) was determined by counting the parasitemia in treated cultures 10 hours after invasion was completed in the control, untreated cultures and comparing it to the parasitemia of the untreated and DMSO-treated control cultures. A parasitemia of 0% indicate that taxol totally inhibits new infections; a parasitemia of 100% indicates that taxol has no effect. The parasitemia were calculated by pooling the results of two separate experiments, with 1000 cells counted at each taxol concentration. DMSO was determined to have no effect on parasite viability or invasion. Parasitemias were identical in untreated and DMSO treated cultures. Taxol reduced the parasitemia of the cultures in a dose dependent fashion. After one replication cycle, 0.5 µM and 1.0 µM taxol reduced the parasitemia by 95% and 100%, respectively. After two cycles, 0.1 µM totally eliminated parasitemia.

Example 6

Cultures of human erythrocytes infected with T9-94 (Thailand, chloroquine resistant and pyrimethamine sensitive) clone of *Plasmodium falciparum* were grown in the absence and presence of taxol as described in Example 2. The infections were synchronized with sorbitol treatment to ±2 hours as described by Lambros and Vanderberg, *J. Parasitol.*, 1979, 65, 418–420. The infections were synchronized with sorbitol treatment to ±2 hours as described by Lambros and Vanderberg, *J. Parasitol.*, 1979, 65, 418–420. Taxol was added 4 hours post-invasion and maintained in cultures for three life cycles. Each life cycle is approximately 48 hours in duration. Parasitemia was measured by examining Giemsa-stained blood smears using a light microscope. The efficacy of taxol, expressed as parasitemia is defined as the number of infected. erythrocytes divided by the total number of erythrocytes X 100. The efficacy of taxol, expressed as Parasitemia (% of control) was determined by counting the parasitemia in treated cultures 10 hours after invasion was completed in the control, untreated cultures and comparing it to the parasitemia of the untreated and DMSO-treated control cultures. A parasitemia of 0% indicate that taxol totally inhibits new infections; a parasitemia of 100% indicates that taxol has no effect. The parasitemia were calculated by pooling the results of two separate experiments, with 1000 cells counted at each taxol concentration. DMSO was determined to have no effect on parasite viability or invasion. Parasitemias were identical in untreated and DMSO treated cultures. Taxol reduced the parasitemia of the cultures in a dose dependent fashion. After one replication cycle, 0.5µM and 1.0µM taxol reduced the parasitemia by 95% and 100%, respectively. After two cycles, 0.5µM totally eliminated parasitemia.

Example 7

Cultures of human erythrocytes infected with 7G8 (Brazil, chloroquine and pyrimethane resistant) clone of *Plasmodium fatciparum* were grown in the absence and presence of taxol as described in Example 2. The infections were synchronized with sorbitol treatment to ±2 hours as described by Lambros and Vanderberg, *J. Parasitol.*, 1979, 65, 418–420. The infections were synchronized with sorbitol treatment to ±2 hours as described by Lambros and Vanderberg, *J. Parasitol.*, 979, 65, 418–420. Taxol was added 4 hours post-invasion and maintained in cultures for three life cycles. Each life cycle is approximately 48 hours in duration. Parasitemia was measured by examining Giemsa-stained blood smears using a light microscope. The efficacy of taxol, expressed as parasitemia is defined as the number of infected erythrocytes divided by the total number of erythrocytes X 100. The efficacy of taxol, expressed as Parasitemia (% of control) was determined by counting the parasitemia in treated cultures 10 hours after invasion was completed in the control, untreated cultures and comparing it to the parasitemia of the untreated and DMSO-treated control cultures. A parasitemia of 0% indicate that taxol totally inhibits new infections; a parasitemia of 100% indicates that taxol has no effect. The parasitemia were calculated by pooling the results of two separate experiments, with 1000 cells counted at each taxol concentration. DMSO was determined to have no effect on parasite viability or invasion. Parasitemias were identical in untreated and DMSO treated cultures. Taxol reduced the parasitemia of the cultures in a dose dependent fashion. After one replication cycle, 0.5µM and 1.0µM taxol reduced the parasitemia by 95% and 100%, respectively. After two cycles, 0.5µM totally eliminated parasitemia.

Example 8

1.0 µM taxol was added to cultures of human erythrocytes infected with FCR3-C5 strain of *P. falciparum* at 8, 16, 24, 28, 32, 34, 36, 38, 40, 42, and 44 hours post-invasion. The parasitemia was counted 10 hours after the end of the first cycle and compared to an untreated control culture. Taxol added up to 30 hours post-invasion completely blocks the formation of new infection. Effectiveness decreased linearly between 30 and 40 hours post-invasion. Taxol added. after 40 hours had no effect on the production of new infections. Examination of Giemsa-stained blood smears taken from the untreated and taxol treated cultures revealed the most striking differences between 42 and 44 hours post-invasion. The untreated cultures contained segmented schizonts, free merozoites and new, ring-stage infections. By contrast, parasites within taxol-treated IRBC often were condensed, the nuclei extremely large and only a few segmented schizonts were visible. Examination of the segmented schizonts by electron microscopy suggested that nuclear division occurred in many of the IRBC in treated cultures. However, compared to untreated IRBC, merozoites were misshapen, their radial distribution was disrupted and the apical orientation of rhoptries and micronemes within the merozoites was often not apparent.

Example 9

Cultures of human erythrocytes infected with the FCR3-C5 strain of *P. falciparum* were treated with 1.0 µM taxol at 8 or 24 hours post invasion. Taxol was removed from the cultures at the time points indicated and the parasitemia was measured 10 hours after re-invasion was complete in an untreated control culture. Taxol added at 24 hours need only be in culture for 8 hours to totally block the formation of new infections.

Example 10

Method for Treating *Pneumocystis carinii* in vitro with Taxol and Taxol Analogs

*P. carinii* is induced in adult male Sprague-Dawley rats by corticosteroid administration and the lungs removed en bloc, minced and homogenized. Erythrocytes are lysed with ammonium chloride solution and the inocula quantitated for the number of *P. carinii* nuclei per ml. Viability is assessed by erythrosin B dye exclusion. *P. carinii* are inoculated into 48 hour old confluent tissue culture cells grown in triplicate 25 ml flasks or 24 well tissue culture plates and incubated in a water jacketed incubator at 37° C. in a 5% $CO_2$ atmosphere. The final numbers of *P. carinii* nuclei in cell culture are approximately $10^7$/ml. A human lung-derived tissue culture cell line A549 (CCL 185) or WI-38, a human embryonic lung fibroblast line are used for culturing *P. carinii*. Medium optimized for *P. carinii* culture contains 20% fetal bovine serum, penicillin. (200 U/ml), streptomycin (200 µg/ml), and amphotericin B (0.5 µg/ml). After inoculation, cultures are sampled on days 1, 3, 5 and 7 by removing 0.1 volume from the flasks or wells and pooling the supernatants. *P. carinii* nuclei are stained with Diff Quik (American Scientific Products, McGaw Park, Ill.) and drops of suspension counted by light microscopy.

Taxol, obtained from Molecular Probes, Inc. (Eugene, Oreg.; catalog # T-3546) is dissolved in dimethyl sulfoxide (DMSO). Cultures of *P. carinii* are either untreated, treated with DMSO only, or treated with taxol to a final concentration of 0.01–1.0 µM. All treated cultures contain the same final concentration of DMSO (0.17%). Taxol is added to the cultures 1 day after inoculation and every other day until 7 days. The effect of taxol on the infection as a function of dose and time is measured by making a slide from the culture and counting the number of nuclei in the cultures every other day. An equal amount of experimental medium is added to replace the amount withdrawn for sampling. The killing of *P. carinii* by taxol is expressed as a peak ratio (ratio of peak organism numbers in treated cultures to peak organism numbers in control cultures). A peak ratio of 1 indicates no effect of taxol; a peak ratio of 0 indicates complete killing of *P. carinii* in the cultures. Typically, 500 to 1000 cells are counted per experiment. Taxol is effective if it prevents the development of sporozoites into multinucleate parasites.

Example 11

Method for Treating Cryptosporidium in vitro with Taxol and Taxol Analogs

*Cryptosporidium* oocytes are cultured in vitro in human fetal lung cells or primary chicken kidney or porcine kidney cells. The culture medium consists of phosphate buffered saline containing 0.1% glucose, penicillin (5000 IU/ml), streptomycin (5 mg/ml), and amphotericin B (20 µg/ml). Sporozoites ($1.5 \times 10^5$) are resuspended in the growth medium in a Leighton tube containing a monolayer of cells growing on a 5 $cm^3$ plastic cover slip. They are incubated for 4 hours at 37° C. in a 5% $CO_2$ atmosphere to allow attachment and penetration of sporozoites. The monolayers are then vigorously washed with tissue culture medium and maintained in a 5% $CO_2$ atmosphere. The formation of different developmental stages (trophozoites, meronts, macrogametes, microgametocytes and oocysts) is assayed by light microscopy.

Cultures infected with *Cryptosporidium* are either untreated or treated with taxol to a final concentration of 0.01–1.0 µM. Taxol is added 4 hours after inoculation and maintained in culture for 1–14 days. The cell medium is changed daily and a fresh aliquot of taxol added with the new medium. The effect of taxol on the infection as a function of dose and time is measured by counting the number of nuclei in the cultures every day. Trophozoites are mononuclear whereas meronts are multinuclear. An equal amount of experimental medium is added to replace the amount withdrawn for sampling. The killing of *Cryptosporidium* by taxol is measured by counting the number of nuclei and examining parasite morphology in the treated cultures and comparing the results to the control, untreated cultures. Typically, 500 to 1000 cells are counted per experiment. Taxol is effective if it prevents the development of sporozoites into multinucleate parasites.

Example 12

Method for Treating Sarcocystis in vitro with Taxol and Taxol Analogs

Motile banana-shaped organisms are obtained by crushing cysts in aseptically excised pieces of leg or breast muscle from wild grackles with a glass tissue grinder. The parasites, suspended in 2–3 ml of Eagle's basal medium with Hanks balanced salt solution (HBME) plus 10% fetal calf serum, are poured through gauze to remove debris and centrifuged at 290 g for 5 minutes. The pelleted parasites are resuspended in tissue culture medium and inoculated into Madin-Darby canine kidney cells or primary cultures of embryonic bovine kidhey or bovine trachea cells. Approximately $5 \times 10^5$ cells are suspended in 2 ml of culture medium and pipetted into Leighton tubes. The tubes are inoculated at 37° C. for 24 hours before inoculation with the parasite and maintained at this temperature for the length of each experiment. Cover slips are removed from the tubes 1–96 hours after inoculation of the parasites. The cells are examined as fresh preparations or fixed in Schaudinn's fluid and stained with Heidenhain's iron hematoxylin. Live parasites are examined by phase contrast microscopy.

Cultures infected with *Sarcocystis* are either untreated or treated with taxol to a final concentration of 0.01–1.0 µM. Taxol is added 4 hours after inoculation and maintained in culture for up to 72 hours. The cell medium is changed daily and a fresh aliquot of taxol added with the new medium. An equal amount of experimental medium is added to replace the amount withdrawn for sampling. The effect of taxol on the infection as a function of dose and time is measured by making slides and counting the number of banana-shaped, ellipsoid and round parasites, multinucleate and cyst-like parasites in the cultures every 6 hours and comparing the results to untreated control cultures. Typically, 500 to 1000 cells are counted per experiment. Taxol is effective if it prevents the development of sporozoites into multinucleate parasites.

Example 13

Method for Treating Isospora in vitro with Taxol and Taxol Analogs

Isospora from the English sparrow, *Passer domesticus*, are developed in primary cultures of embryonic chick and canary cells grown in Leighton tubes in Medium 199, Hanks base with 10% calf serum. The Leighton tubes contain 10.5×35 mm cover slips and are each inoculated with 0.8 ml of a cell suspension containing $1.6 \times 10^6$ cells. Approximately 4 hours after adding sporozoites to the Leighton tubes, the cells are washed two times with 0.8 ml of growth medium 199 and the same quantity of growth medium is added. The medium is thereafter changed daily.

Cultures infected with *Isospora* are either untreated or treated with taxol to a final concentration of 0.01–1.0 µM. Taxol is added 4 hours after inoculation and maintained in culture for up to 72 hours. The cell medium is changed daily and a fresh aliquot of taxol added with the new medium. An equal amount of experimental medium is added to replace the amount withdrawn for sampling. The effect of taxol on the infection as a function of dose and time is measured by making slides and counting the number of infected cells and the number of nuclei in the cultures every 6 hours and comparing the results to untreated control cultures. Typically, 500 to 1000 cells are counted per experiment. Coverslips removed for counting cells are fixed with formalin and stained with Harris hematoxylin and counter stained with Putts' eosin. Taxol is effective if it prevents the development of sporozoites into multinucleate parasites.

Example 14

Effect of Taxol on DNA Synthesis.

Figure 1:
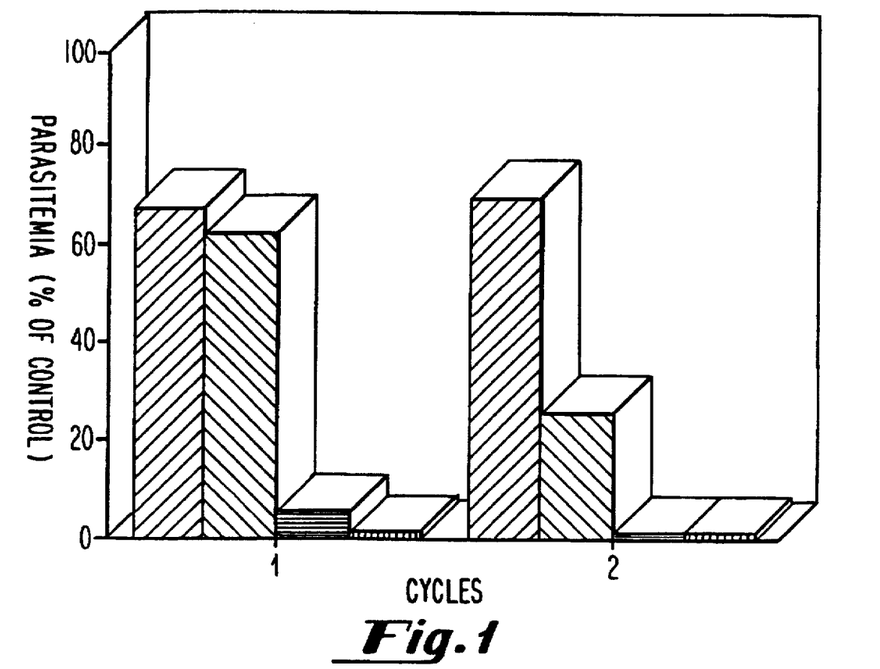
FIG. 1 is a schematic representation of the effect of taxol on human erythrocytes infected with drug sensitive FCR3-C5 malaria clones. Cultures of infected erythrocytes were either untreated, treated with DMSO only (data not shown), or treated with taxol to a final concentration 0.05 uM, horizontal striped bars; 0.1 uM, solid black bars; 0.5 uM, diagonal, striped bars; or 1.0 uM, vertical hatched bars.
Figure 2:
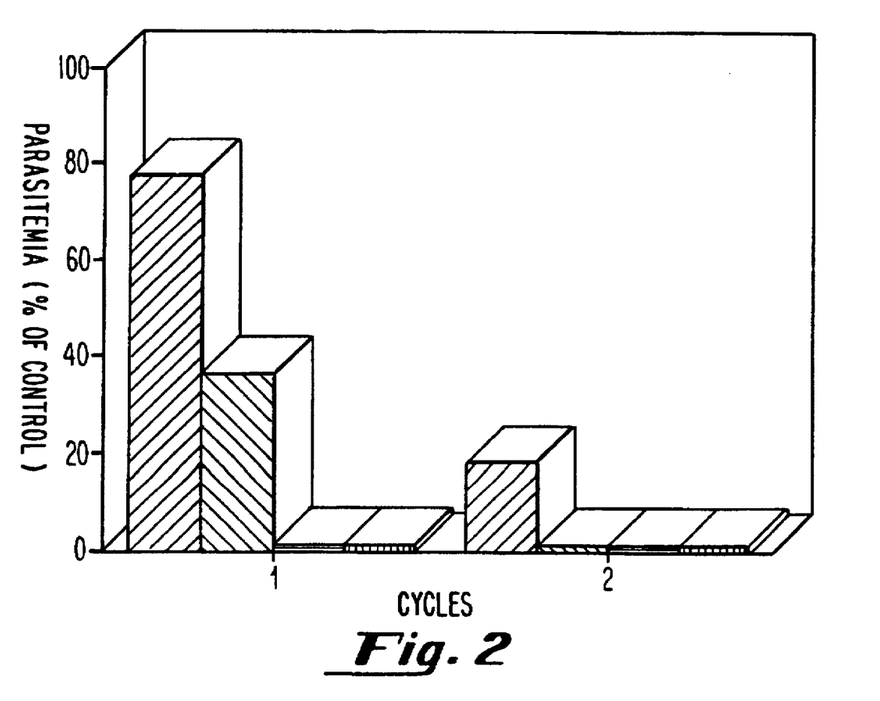
FIG. 2 is a schematic representation of the effect of taxol on chloroquine sensitive, pyrimethamine resistant HB3 malaria clones. Cultures of infected erythrocytes were either untreated, treated with DMSO only (data not shown), or treated with taxol to a final concentration 0.05 uM, horizontal striped bars; 0.1 uM, solid black bars; 0.5 uM, diagonal, striped bars; or 1.0 uM, vertical hatched bars.
Figure 3:
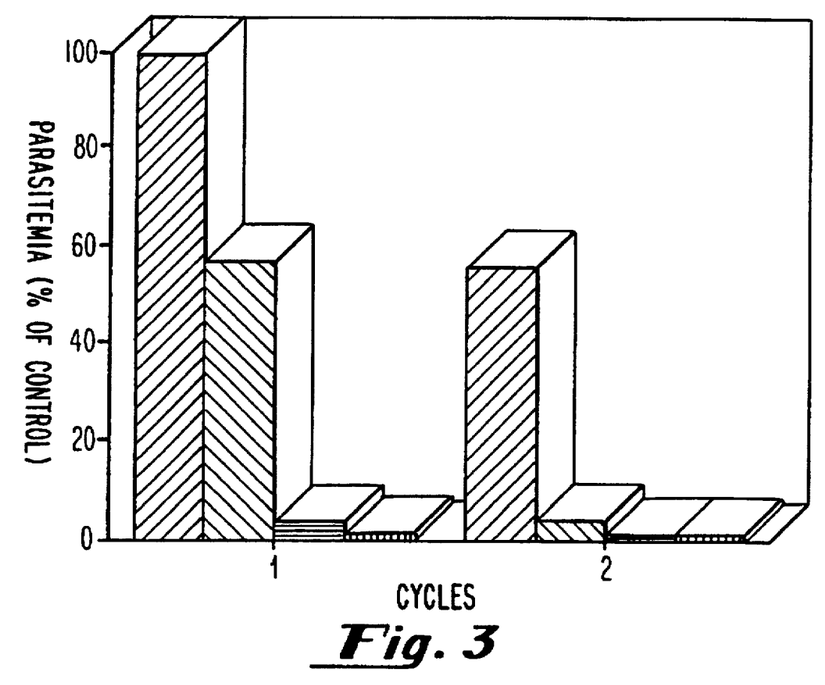
FIG. 3 is a schematic representation of the effect of taxol on chloroquine resistant, pyrimethamine sensitive T9-94 malaria clones. Cultures of infected erythrocytes were either untreated, treated with DMSO only (data not shown), or treated with taxol to a final concentration 0.05 uM, horizontal striped bars; 0.1 uM, solid black bars; 0.5 uM, diagonal, striped bars; or 1.0 uM, vertical hatched bars.
Figure 4:
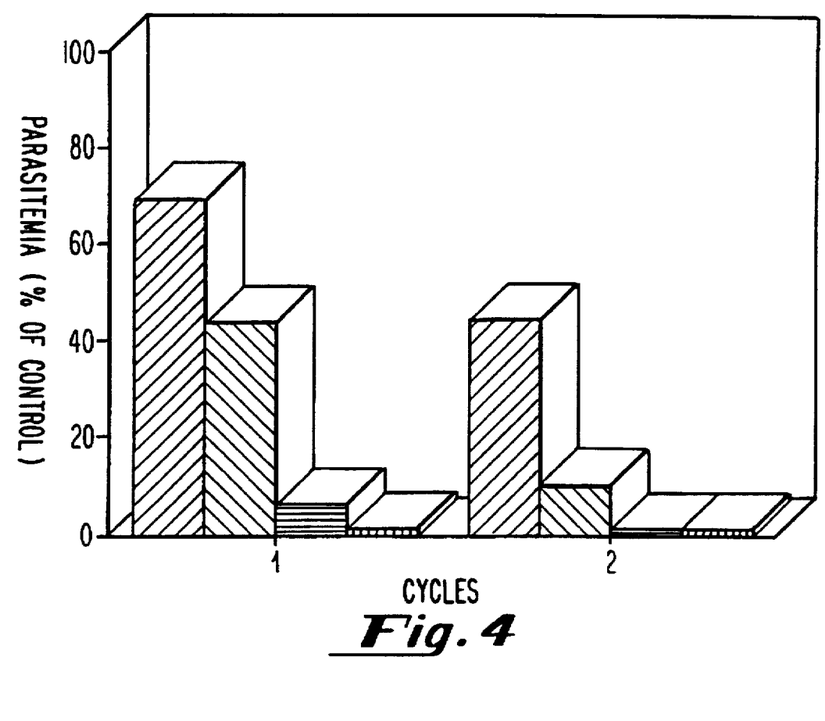
FIG. 4 is a schematic representation of chloroquine resistant, pyrimethamine resistant, 7G8 malaria clones. Cultures of infected erythrocytes were either untreated, treated with DMSO only (data not shown), or treated with taxol to a final concentration 0.05 uM, horizontal striped bars; 0.1 uM, solid black bars; 0.5 uM, diagonal, striped bars; or 1.0 uM, vertical hatched bars.
Figure 5:
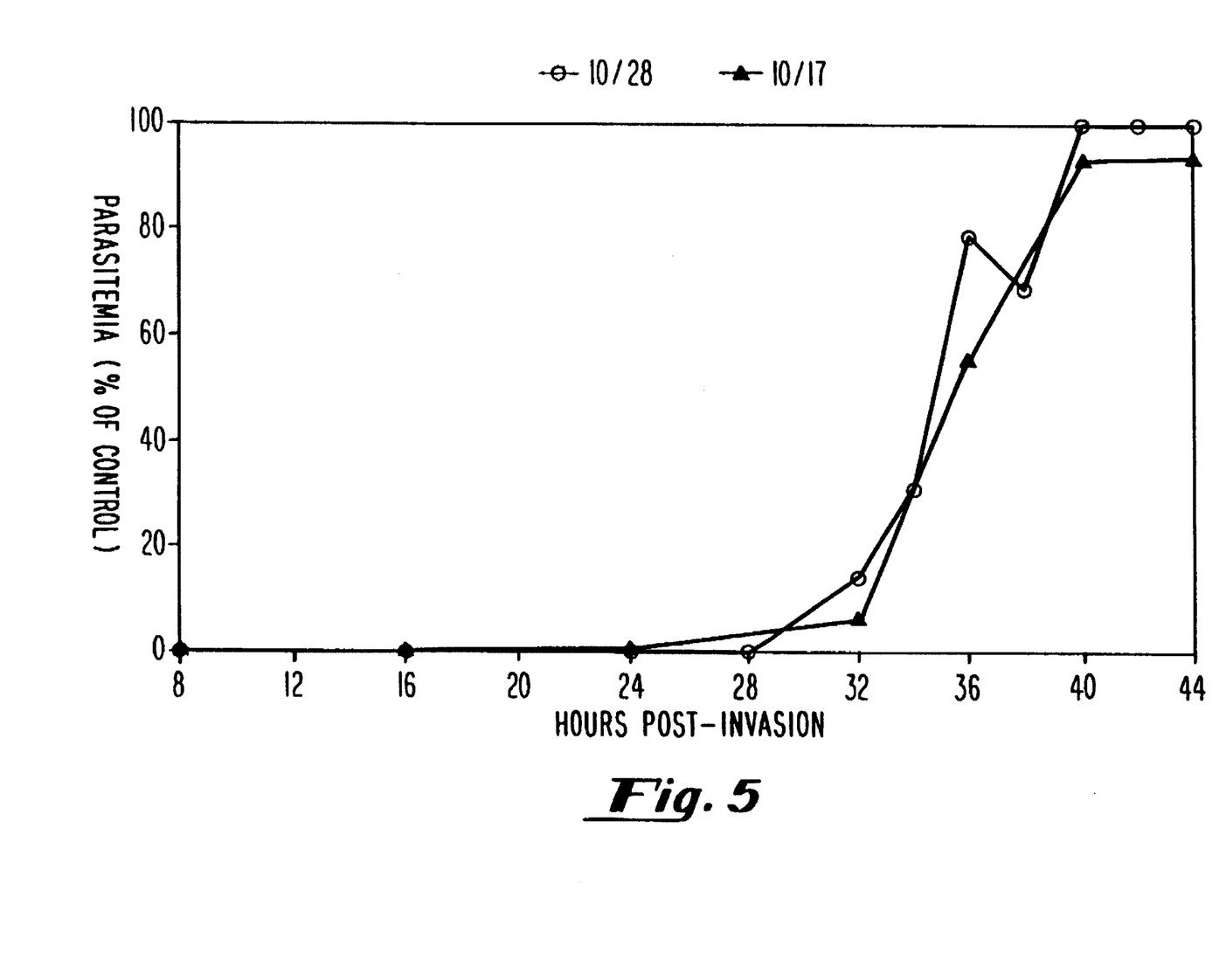
FIG. 5 is a schematic representation of the time course of taxol treatment necessary for the inhibition of new infections after 1 life cycle.
Figure 6:
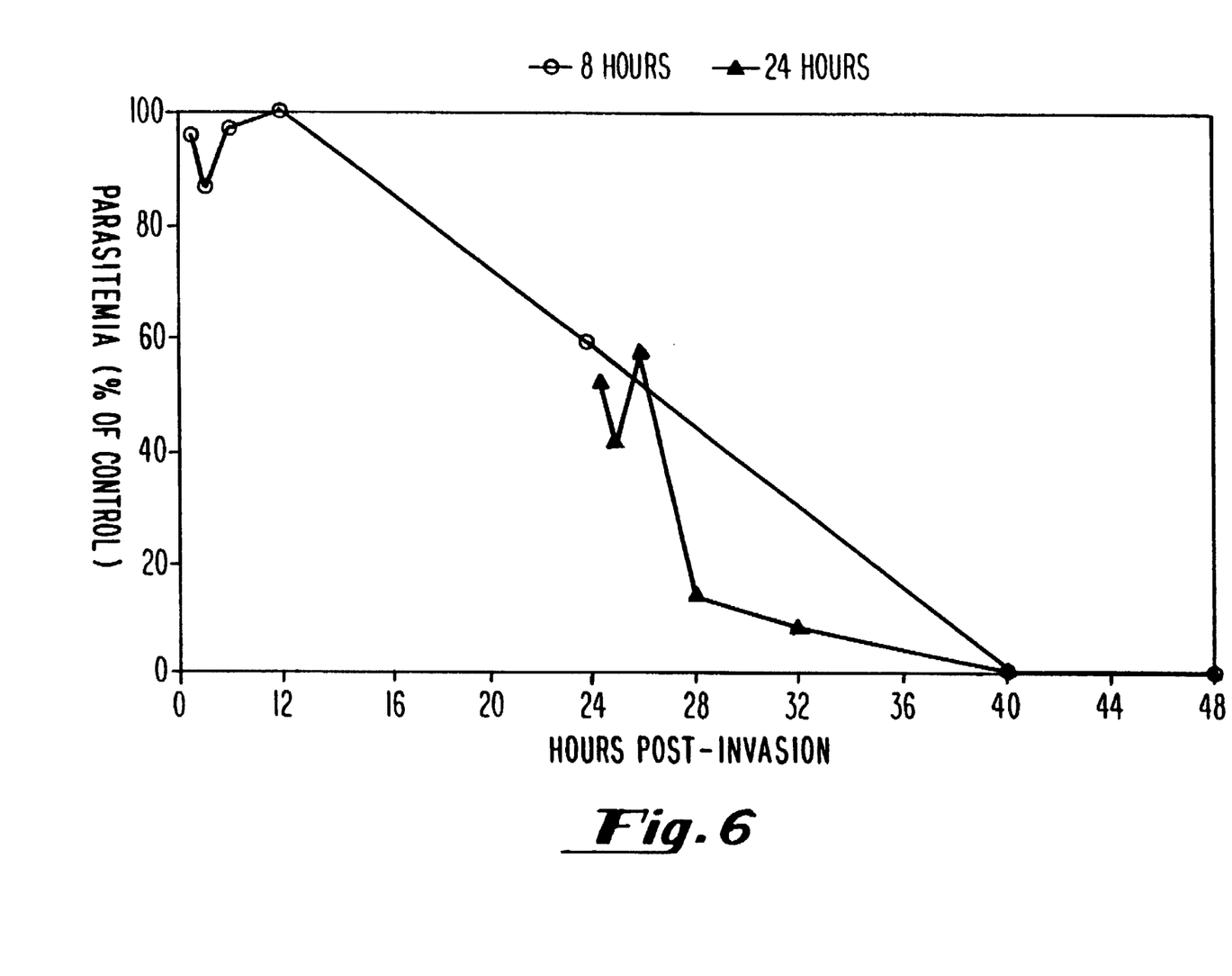
FIG. 6 is a schematic representation of the duration of taxol treatment necessary for the inhibition of new infections.
Figure 7:
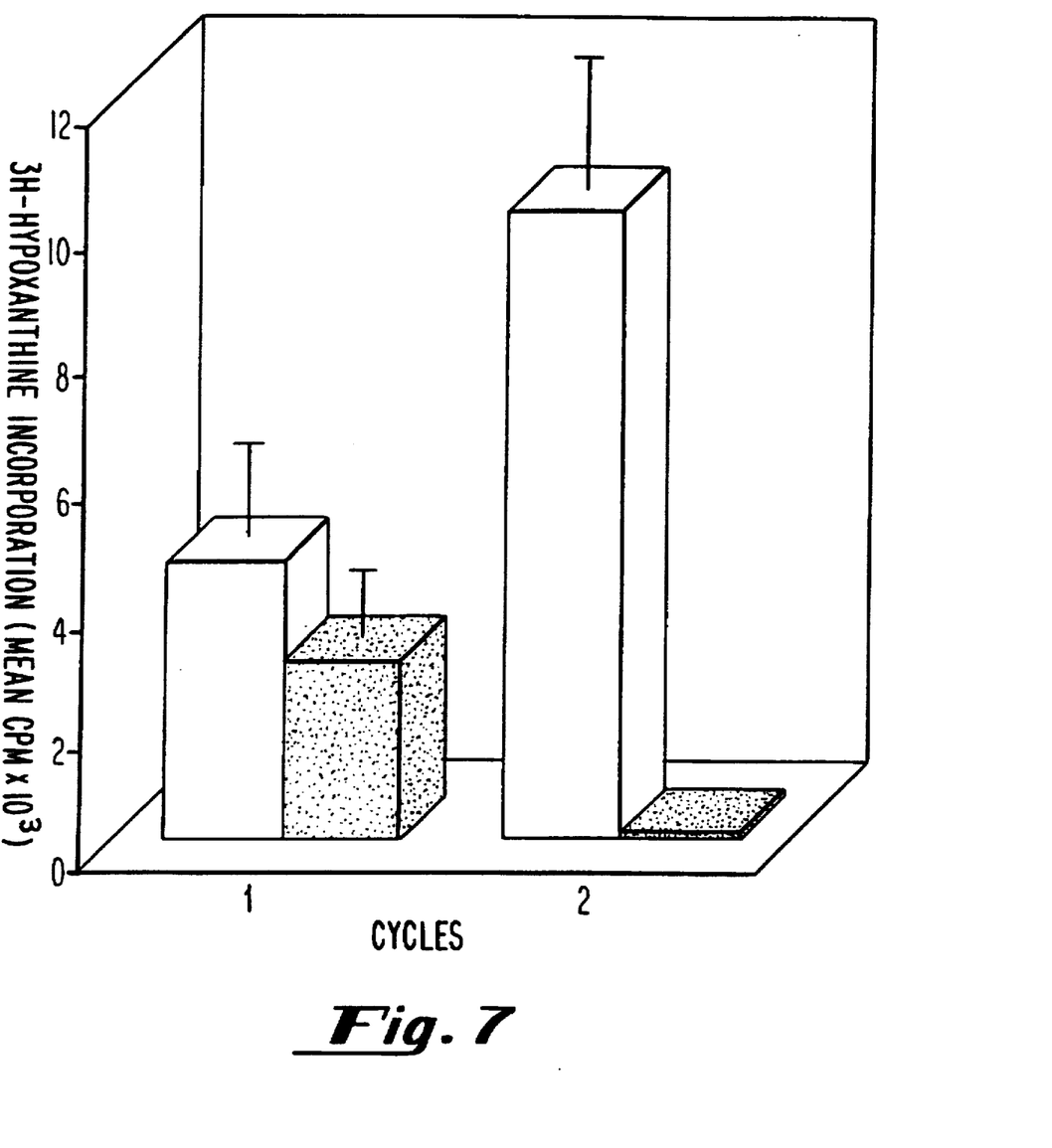
FIG. 7 is a schematic representation of the effect of taxol on parasite viability. Open bars represent untreated cultures and filled bars represent taxol-treated cultures.

The effect of taxol on parasite viability was assessed by measuring the incorporation of $^3$H-hypoxanthine into untreated and treated cultures. Highly synchronous (±2h)

cultures of FCR3-C5-infected erythrocytes were grown in a 96 well plate. Each well contained 3 µl of IRBC at a parasitaemia of 1–2 %, 90 µl of hypoxanthine-free culture medium and 10 µl of human serum. Eight wells were untreated and eight wells treated with 1.0 µM taxol at 4 h post-invasion. The culture medium in each well was replaced with taxol-free, hypoxanthine-free medium after the first cycle. During the trophozoite stage (32 h post-invasion) of the first cycle, 18 µl of culture medium containing $^3$H-hypoxanthine (Amersham, 1–5 Ci/mmol) at 20 uCi/ml and 2 µl of human serum was added to half of the wells for 4 h. The same additions were made at the trophozoite stage, of the second cycle to the remaining wells. The radioisotopically labeled cultures were harvested onto glass fiber filters (Whatman, Inc.) using distilled water and an automated cell harvester (Cambridge Technology, Inc.). The filters were added to 10.0 ml of BioSafe II and counted in a liquid scintillation counter. Values shown are the mean of four measurements. $^3$H-hypoxanthine into control or taxol-treated cultures was similar during the first cycle. No incorporation of $^3$H-hypoxanthine was detected in the treated cultures during the second cycle. See FIG. 7. Thus, taxol appears to act by preventing the establishment of new infections.

Example 15

Determination of Parasite Recrudescence

Figure 8:
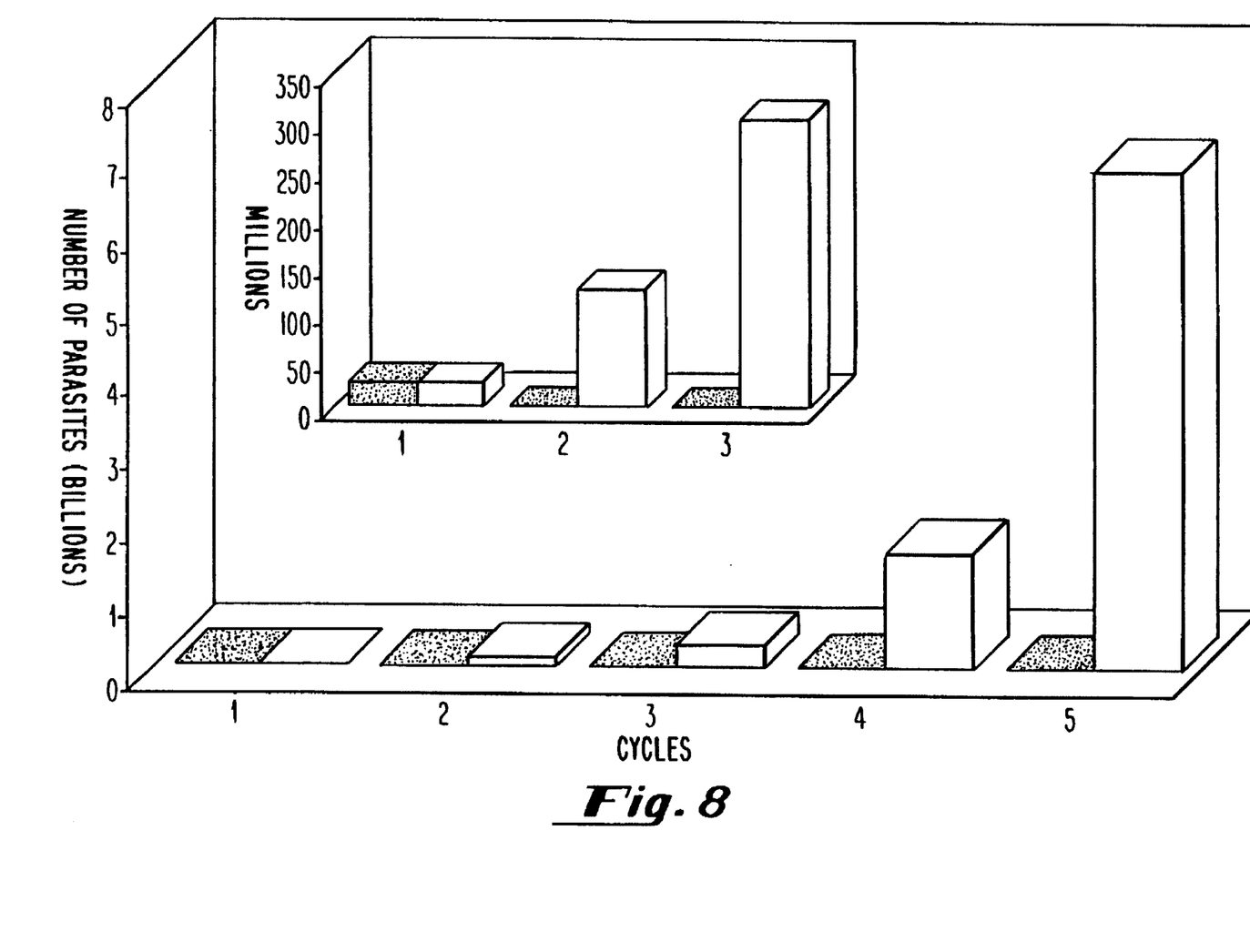
FIG. 8 is a schematic representation of the effect of taxol on parasite recrudescence. The infection disappeared in the treated culture (black bars) after the first cycle, while in the control culture (white bars) there was a 276-fold increase in the number of parasites after 4 additional cycles. Insert. To more clearly discriminate differences in parasitaemia between treated and untreated cultures during the first 3 replication cycles, the number of parasites is expressed in millions.

To determine if the infections in taxol-treated cultures were recrudescent, two cultures at 5% hematocrit containing $2.5 \times 10^7$ IRBC were established. When the parasites were young rings, 1.0 µM taxol (4.3 µl of taxol in DMSO) was added to one culture and 4.3 µl of DMSO to the other. After reinvasion, the medium was changed in both cultures to remove the taxol and/or DMSO. The cultures were maintained for 8 days corresponding to 4 additional cycles. The parasitaemias were counted after each cycle of re-invasion. The parasitaemia of the control culture was kept below 5% by the addition of fresh blood. When the cultures were grown for 3 additional cycles, the parasitemia increased nearly three hundred times in the untreated culture while no IRBC were detected in the taxol treated culture. See FIG. 8.

Example 16

Treatment of *Plasmodium chabaudi adami*-infected Mice with Taxol

Figure 9:
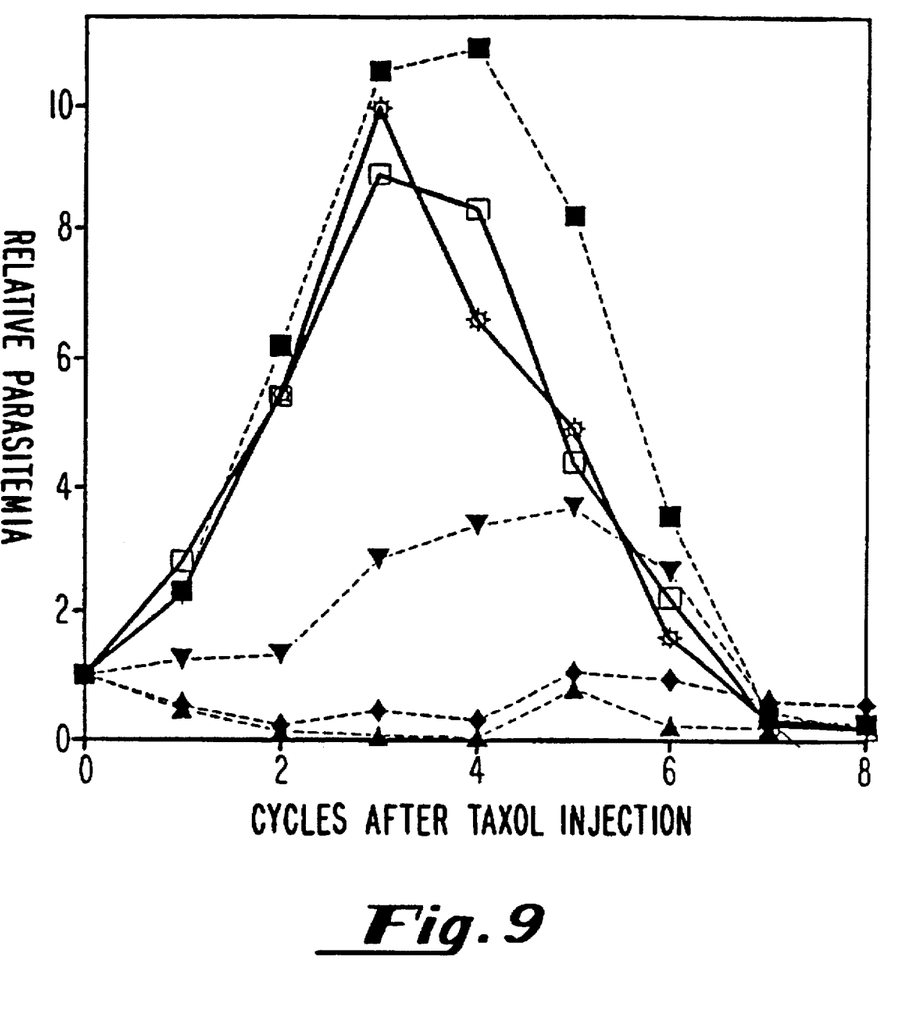
FIG. 9 is a schematic representation of the reduction and clearance of parasitemia in mice infected with *Plasmodium chabuadi adami* by a single injection of taxol. Taxol at 150 mg/m² was given to different groups of infected mice at 2 h intervals (4 p.m.,▲; 6 p.m.,♦; 8 p.m.,▼; 10 p.m., ■). One group of control mice (□) was treated identically as the treated groups except that taxol was omitted from the formulation. The other control group (sunbursts) received saline.
Figure 10:
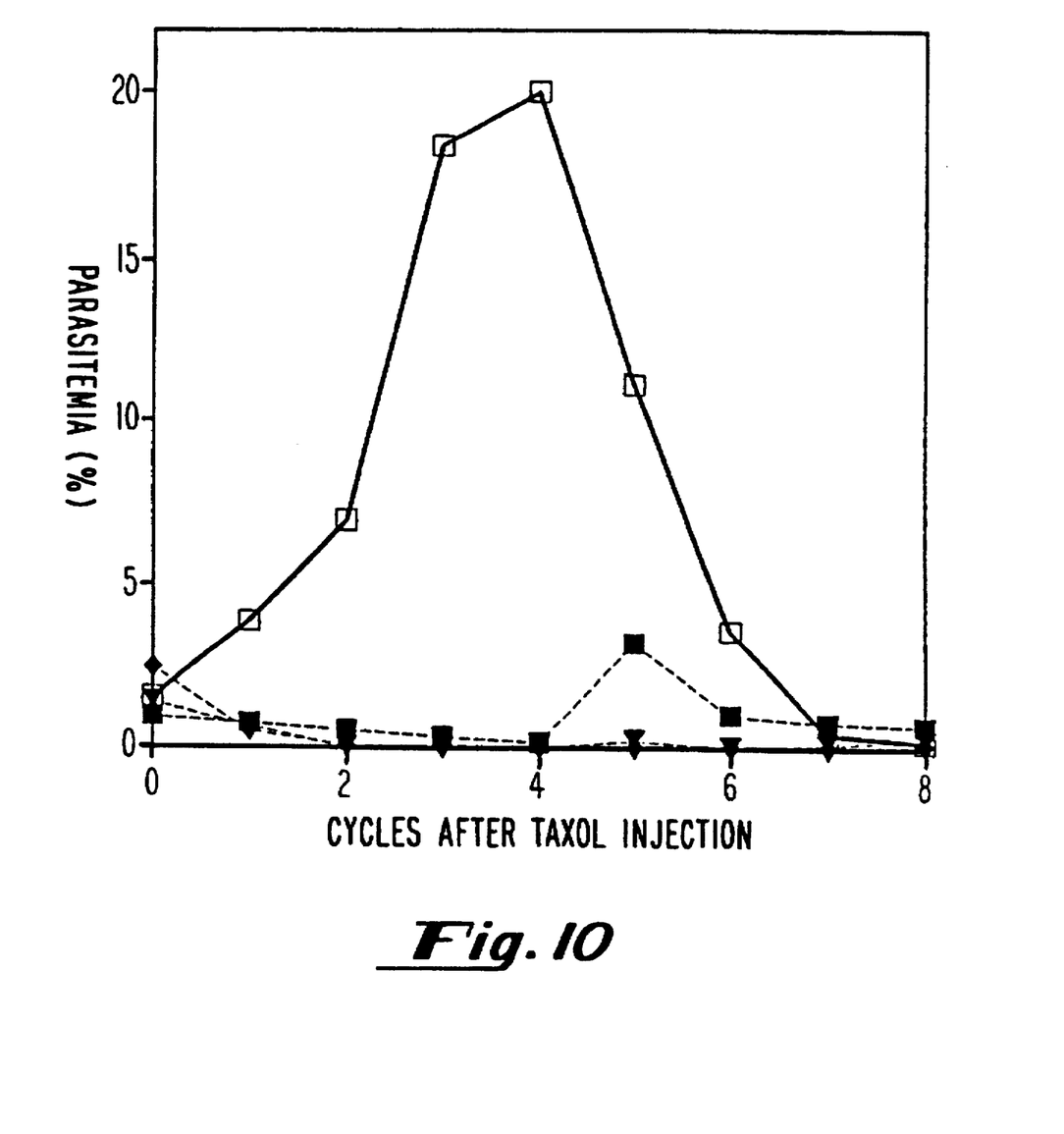
FIG. 10 is a schematic representation of the reduction and clearance of parasitemia in individual mice (■, ♦, ▼) in the 4 P.M. group. A cremophor-treated, control mouse (□) is shown for comparison.

Thirty, seven week old male BALB/c ByJ mice (Jackson Laboratories) were administered intraperitoneal injections of $2.0 \times 10^5$ Plasmodium chabaudi adami parasites. The parasitaemias, which were estimated from tail vein blood smears, were allowed to reach a mean of 1–2% before beginning the experiment. Seven to ten days were required for the parasitaemias to reach these levels. One life cycle is completed in 24 h. Taxol, obtained from the Thomas Jefferson University Hospital pharmacy, is supplied in an ampoule at 6 mg/ml in 5.0 ml of 1:1, v/v, of polyethoxylated castor oil (Cremophor EL) and dehydrated alcohol. On day 0, eight groups of mice (each group contained 3 animals) were given a single, 1.0 ml intraperitoneal injection of taxol at 150 or 75 mg/m$^2$ at 2 h intervals beginning at the mid-trophozoite stage (4 p.m.). The highest dosage was chosen by extrapolating the LD$^{10}$ for a single i.p. taxol injection in rats to mice. National Cancer Institute Clinical Brochure: Taxol (NSC 125973) pp. 1–36. Bethesda, Md.: Division of Cancer Treatment, National Cancer Institute, July 1991. Conversion from mg/m$^2$ to mg/kg is based on the empirical correlation that surface area (m$^2$)=K-W$^{2/3}$/100, where K is a species-specific factor and W is body weight in kg. Freireich, et al., *Cancer Chemother. Rep.*, 1966, 50, 219–244. K is 9 for rats and mice and 10.6 for a 70 kg human. A dose at 150 mg/m$^2$ is equivalent to 975 ug in a 20 g mouse and 260 mg in a 70 kg human. The injections consisted of the desired volume of the stock taxol solution adjusted to 1.0 ml with saline. One group of control mice was treated identically as the treated groups except that taxol was omitted from the formulation. The other control group received saline. Daily blood smears were made over 8 life cycles and the parasitaemia measured to assess the effect of the treatment. Mean values were obtained for each group daily and divided by the mean value on day 0. This is defined as the relative parasitaemia. The parasitemia in the saline and cremophor control groups increased after each of the first four cycles of infection, however, the groups treated with 150 mg/m$^2$ of taxol at 4 or 6 pm. exhibited a dramatic decrease after the first cycle (FIGS. 9 and 10). Parasitaemia was completely cleared in 2 of the mice in the 4 p.m. group, and drastically reduced in the third after 2 cycles. Parasitaemia was also greatly reduced in the group injected at 6 p.m., although no animals were completely cured. Taxol administered at the lower dose of 75 mg/m$^2$ only slightly reduced parasitaemia (data not shown). The parasitaemia decreased in the untreated groups after 3–4 cycles as a result of a natural immune response in the mice.

What is claimed is:

1. A method of inhibiting the proliferation of a protozoal parasite comprising contacting the protozoal parasite with an amount of taxol or taxol analog effective to inhibit the proliferation of said parasite wherein said parasite is selected from the group consisting of *Babesia, Pneumocystis, Cryptosporidium, Sarcocystis, Isospora,* and *Toxoplasma*.

2. The method of claim 1 wherein the parasite is contacted with from about 0.1 µM to about 1 µM taxol or taxol analog.

3. The method of claim 1 wherein the period of contact is from about 8 to about 48 hours.

4. The method of claim 1 wherein said taxol analog is taxotere.

5. A method of inhibiting the asexual reproduction of a Sporozoa protozoal parasite comprising contacting the protozoal parasite with an amount of taxol or taxol analog effective to inhibit the reproduction of said parasite.

6. The method of claim 5, wherein said Sporozoa parasite is selected from the group consisting of *Plasmodium, Babesia, Pneumocystis, Cryptosporidium, Sarcocystis, Isospora,* and *Toxoplasma*.

* * * * *

UNITED STATES PATENT AND TRADEMARK OFFICE
CERTIFICATE OF CORRECTION

PATENT NO. : 5,631,278
DATED : May 20, 1997
INVENTOR(S) : Theodore F. Taraschi and Bruno Pouvelle It is certified that error appears in the above-indentified patent and that said Letters Patent is hereby corrected as shown below:

Col. 1, line 59, "Glossind" should be --Glossina--.
Col. 8, line 38, "HB2!" should be --HB3--.
Col. 9, line 48, "979" shuld be --1979--.
Col. 12, line 4, "kidhey" should be --kidney--.

Signed and Sealed this

Ninth Day of September, 1997

Attest:

BRUCE LEHMAN

*Attesting Officer*     *Commissioner of Patents and Trademarks*